United States Patent
Mei et al.

(10) Patent No.: US 9,560,975 B2
(45) Date of Patent: *Feb. 7, 2017

(54) THREE DIMENSIONAL ELECTRONIC PATCH

(71) Applicant: VivaLnk Limited (Cayman Islands), Santa Clara, CA (US)

(72) Inventors: Junfeng Mei, Sunnyvale, CA (US); Zhigang Wang, Fremont, CA (US)

(73) Assignee: VivaLnk Limited (Cayman Islands), Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/274,119

(22) Filed: Sep. 23, 2016

(65) Prior Publication Data

US 2017/0007133 A1    Jan. 12, 2017

Related U.S. Application Data

(63) Continuation of application No. 14/814,347, filed on Jul. 30, 2015, now Pat. No. 9,483,726.

(60) Provisional application No. 62/089,845, filed on Dec. 10, 2014.

(51) Int. Cl.
| | |
|---|---|
| *G01K 13/00* | (2006.01) |
| *A61B 5/01* | (2006.01) |
| *G06K 19/077* | (2006.01) |
| *A61B 5/00* | (2006.01) |
| *H01Q 7/00* | (2006.01) |
| *H01Q 1/22* | (2006.01) |

(52) U.S. Cl.
CPC .............. *A61B 5/01* (2013.01); *A61B 5/0008* (2013.01); *A61B 5/6814* (2013.01); *A61B 5/6833* (2013.01); *G06K 19/0776* (2013.01); *G06K 19/07773* (2013.01); *H01Q 1/2225* (2013.01); *H01Q 7/00* (2013.01)

(58) Field of Classification Search
CPC combination set(s) only.
See application file for complete search history.

(56) References Cited

U.S. PATENT DOCUMENTS

| | | | |
|---|---|---|---|
| 6,952,085 B2 | 10/2005 | Nerone | |
| 9,483,726 B2 * | 11/2016 | Mei | G06K 19/07773 |
| 2007/0270672 A1 | 11/2007 | Hayter | |
| 2008/0167572 A1 | 7/2008 | Stivoric | |
| 2009/0171180 A1 | 7/2009 | Pering | |
| 2012/0242481 A1 | 9/2012 | Gernandt | |
| 2014/0121557 A1 | 5/2014 | Gannon et al. | |

FOREIGN PATENT DOCUMENTS

WO    2010023255 A1    10/2013

* cited by examiner

*Primary Examiner* — Christle I Marshall
(74) *Attorney, Agent, or Firm* — SV Patent Service

(57) ABSTRACT

A three-dimensional electronic patch includes a flat flexible circuit substrate that includes an elastic layer including a first portion and a second portion. The second portion includes at least side connected to the elastic layer and one or more sides defined by one or more cuts in the elastic layer. The three-dimensional electronic patch further includes a first sensor on the first portion of the elastic layer, a first conductive sensing pad under the first portion of the elastic layer and in electrical connection with the first sensor, and a conductive layer under the second portion of the elastic layer and in electrical connection with the first sensor. The second portion is folded to position the conductive layer away from the first portion.

21 Claims, 6 Drawing Sheets

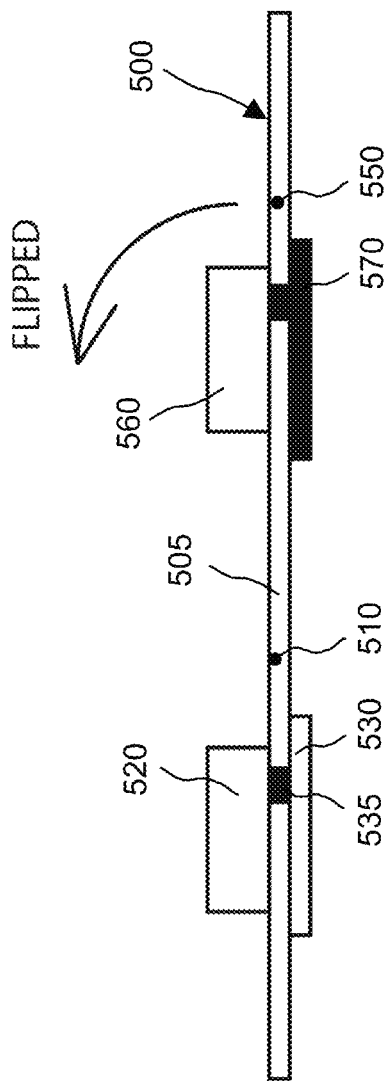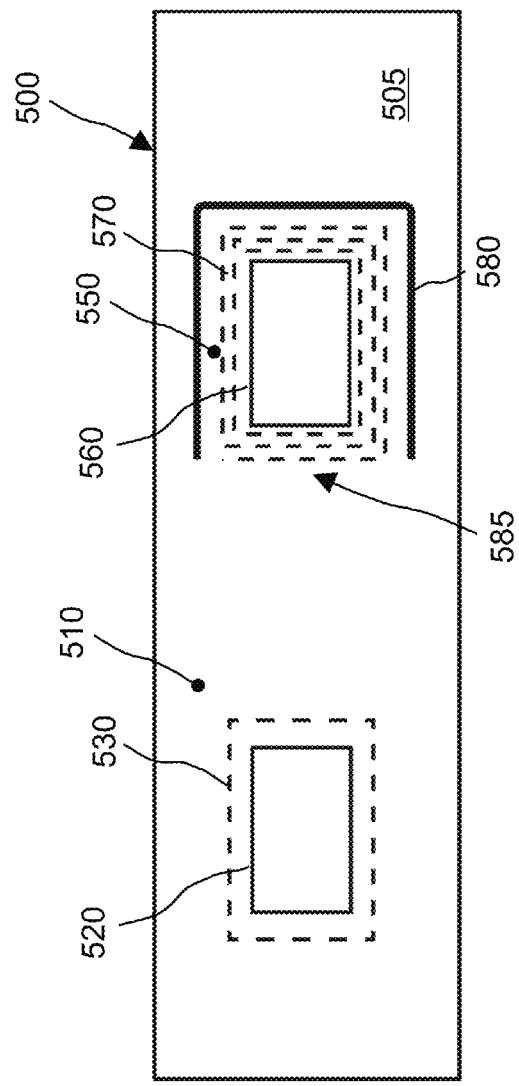
Figure 5A
Figure 5B

THREE DIMENSIONAL ELECTRONIC PATCH

BACKGROUND OF THE INVENTION

The present application relates to electronic devices, and in particular, to electronic patches that can adhere to human skin or the surface of an object.

Electronic patches or stickers can be attached to human bodies and other objects such as merchandized goods such as computers, machineries, and clothes, packaging material and shipping boxes. Electronic patches can communicate with smart phones or other devices wirelessly, through NFC, Bluetooth, WiFi, or other methods. Tags wearable by people are a specific type of electronic patches.

Electronic patches can be used for tracking objects and for performing functions such as producing sound, light or vibrations, and so on. As the applications and human needs become more sophisticated and complex, there are a rapidly increasing number of tasks that electronic patches are required to perform. Electronic patches are often required to be conformal to curved surfaces. In addition, the curvature of the human skin can vary overtime.

Electronic patches and wearable tags can communicate with smart phones and other devices using WiFi, Bluetooth, Near Field Communication (NFC), and other wireless technologies. NFC is a wireless communication standard that enables two devices to quickly establish communication within a short range around radio frequency of 13.56 MHz. NFC is more secure than other wireless technologies such as Bluetooth and Wi-Fi because NFC requires two devices in close proximity (e.g. less than 10 cm). NFC can also lower cost comparing to other wireless technologies by allowing one of the two devices to be passive (a passive NFC tag).

Bluetooth is another wireless technology standard for exchanging data over relatively longer distances (in tens of meters). It employs short wavelength UHF radio waves from 2.4 to 2.485 GHz from fixed or mobile devices. Bluetooth devices have evolved to meet the increasing demand for low-power solutions that is required for wearable electronics. Benefited from relatively longer reading distance and active communication, Bluetooth technologies allow wearable patches to continuously monitoring vital information without human interference, which is an advantage over NFC in many applications.

Wearable patch (or tag) is an electronic patch to be worn by a user. A wearable patch is required to stay on user's skin and operate for an extended period of time from hours to months. A wearable patch can contain a micro-electronic system that can be accessed using NFC, Bluetooth, WiFi, or other wireless technologies. An authentication wearable tag can be used as a "password" similar to a barcode. For example, it can recognize a user's smart phone for authentication purpose. A wearable patch can also be integrated with different sensors such as vital signs monitoring, motion track, skin temperature measurements, and ECG detection.

Despite recent development efforts, conventional wearable devices still face several drawbacks: they may not provide adequate comfort for users to wear them; they may not stay attached to user's body for the required length of time; they are usually not aesthetically appealing.

A wearable patch often includes multiple rigid semiconductor chips and sensors have significant thicknesses assembled on flexible printed circuits to provide sensor, computation, and communication functions. The printed circuits are typically made of flexible polymer substrates that are not deformable enough to adapt to commonly occurring shape change, the high percentage of deformations of the user's skin, which is one reason for users' discomfort when they wear these wearable patches.

Another drawback of conventional wearable patches is that the rigid polymer substrate is not very breathable. The build-up of sweat and moisture can cause discomfort and irritation to the skin, especially after wearing it for an extended period of time.

Moreover, conventional wearable patches are often not robust enough to sustain repeated elongations during body movements. Under stress, different layers in wearable patches can break or delaminate rendering the wearable patches inoperable.

Another challenge for wearable patches is that the wearer's skin may interfere with their proper operations. For example, when an antenna is placed in contact with the skin, the antenna's communication range is significantly reduced. In one example, the wireless communication range of an antenna in contact with the skin is less than half the range if the antenna is placed just 4 mm away from the user's skin.

In addition, while some sensors such as electroencephalogram (EEG) and body temperature sensors need to be in contact of users' skins to conduct measurements, other sensors such as ambient temperature sensor are required to measure signals away from the user's skin. The ambient temperature if often different from the human body temperature that is in the range of 36-41° C.

There is therefore a need for more flexible wearable electronic patches that stick to skin longer, are comfortable for users to wear, and can perform intended functions at and away from users' skins so it is not affected by body temperature.

SUMMARY OF THE INVENTION

The presently disclosure attempts to address the aforementioned limitations in conventional electronic patches. The disclosed electronic patches are highly compliant and more stretchable, while also being able to support the circuit, chips, and other electronic components in the wearable electronic patches. The disclosed electronic patches can change their physical shape and dimension to relieve stresses such as repeated elongations, therefore increasing durability. The disclosed electronic patches can stay attached to skin for longer period of time enduring muscle movements while providing constant contact to the skin.

The disclosed electronic patches are also breathable. The stretchability and the breathability make the disclosed electronic patches more comfortable for the users.

Importantly, the disclosed electronic patches are capable wireless communication with little interference from users' skins. Moreover, the disclosed electronic patches can conduct measurements both at users' skins and away from the user's skin. The present application further discloses simple and effective manufacturing process to fabricate such wearable electronic patches.

In one general aspect, the present invention relates to a three-dimensional electronic patch that includes a flat flexible circuit substrate comprising an elastic layer including a first portion and a second portion, wherein the second portion includes at least side connected to the elastic layer and one or more sides defined by one or more cuts in the elastic layer; a first sensor on the first portion of the elastic layer; a first conductive sensing pad under the first portion of the elastic layer and in electrical connection with the first sensor; and a conductive layer under the second portion of the elastic layer and in electrical connection with the first sensor, wherein the second portion can be folded to position the conductive layer away from the first portion.

Implementations of the system may include one or more of the following. The first conductive sensing pad and the conductive layer of the folded second portion can be respectively on opposing sides of the three-dimensional electronic patch. The three-dimensional electronic patch can further include a second sensor on the second portion of the elastic layer and in electrical connection with the conductive layer, wherein the conductive layer includes a second conductive sensing pad electrically connected with the second sensor. The second sensor can measure ambient temperature via the second conductive sensing pad. The second conductive sensing pad and the second sensor can be electrically connected by a conductive pin through the second portion of the elastic layer. The three-dimensional electronic patch can further include an adhesive layer configured to bond the second sensor to the first portion of the elastic layer. The first conductive sensing pad can be in contact with a user's skin, wherein the first sensor is configured to measure body temperature of a user via the first conductive sensing pad. The first conductive sensing pad and the first sensor can be electrically connected by a conduct pin through the first portion of the elastic layer. The conductive layer can include an antenna circuit. The three-dimensional electronic patch can further include a spacer on the second portion of the elastic layer, wherein the spacer is configured to keep the conductive layer at a distance away from the conductive sensing pad while the second portion is folded to be in parallel to the first portion. The three-dimensional electronic patch can further include an adhesive layer configured to bond the spacer to the first portion of the elastic layer. The antenna circuit can be electrically connected with the first sensor by a circuit in or on the elastic layer. The antenna circuit can transmit wireless signals to transfer sensing data measured by the first sensor.

In another general aspect, the present invention relates to a three-dimensional electronic patch that includes a flat flexible circuit substrate comprising: an elastic layer including a first portion and a second portion, wherein the second portion includes at least side connected to the elastic layer and one or more sides defined by one or more cuts in the elastic layer; a first sensor on the first portion of the elastic layer; a first conductive sensing pad under the first portion of the elastic layer and in electrical connection with the first sensor, wherein the first conductive sensing pad is configured to be in contact with a user's skin, wherein the first sensor is configured to measure body temperature of a user via the first conductive sensing pad; a second sensor on the second portion of the elastic layer; and a second conductive sensing pad under the second portion of the elastic layer and in electrical connection with the second sensor, wherein the second sensor is configured to measure ambient temperature via the second conductive sensing pad, wherein the second portion is folded to position the second conductive sensing pad away from the first portion.

Implementations of the system may include one or more of the following. The first conductive sensing pad and the second conductive sensing pad of the folded second portion can be respectively on opposing sides of the three-dimensional electronic patch. The first conductive sensing pad and the first sensor can be electrically connected by a conduct pin through the elastic layer, wherein the second conductive sensing pad and the second sensor are electrically connected by a conductive pin through the second portion of the elastic layer. The three-dimensional electronic patch can further include an adhesive layer configured to bond the second sensor to the first portion of the elastic layer.

In another general aspect, the present invention relates to a three-dimensional electronic patch that includes a flat flexible circuit substrate comprising: an elastic layer including a first portion and a second portion, wherein the second portion includes at least side connected to the elastic layer and one or more sides defined by one or more cuts in the elastic layer; a first sensor on the first portion of the elastic layer; a first conductive sensing pad under the first portion of the elastic layer and in electrical connection with the first sensor; and an antenna circuit under the second portion of the elastic layer and in electrical connection with the first sensor, wherein the second portion is folded to position the antenna circuit away from the first portion.

Implementations of the system may include one or more of the following. The first conductive sensing pad and the antenna circuit of the folded second portion are respectively on opposing sides of the three-dimensional electronic patch. The three-dimensional electronic patch can further include a spacer on the second portion of the elastic layer, wherein the spacer is configured to keep the conductive layer at a distance away from the conductive sensing pad while the second portion is folded to be in parallel to the first portion. The three-dimensional electronic patch can further include an adhesive layer configured to bond the spacer to the first portion of the elastic layer. The antenna circuit is configured to transmit wireless signals to transfer sensing data measured by the first sensor.

These and other aspects, their implementations and other features are described in detail in the drawings, the description and the claims.

BRIEF DESCRIPTION OF THE DRAWINGS

FIGS. 5A and 5B are respectively a cross-sectional and a top view of an exemplified flat flexible circuit substrate including an antenna for wireless communications.

DETAILED DESCRIPTION OF THE INVENTION

Figure 1:
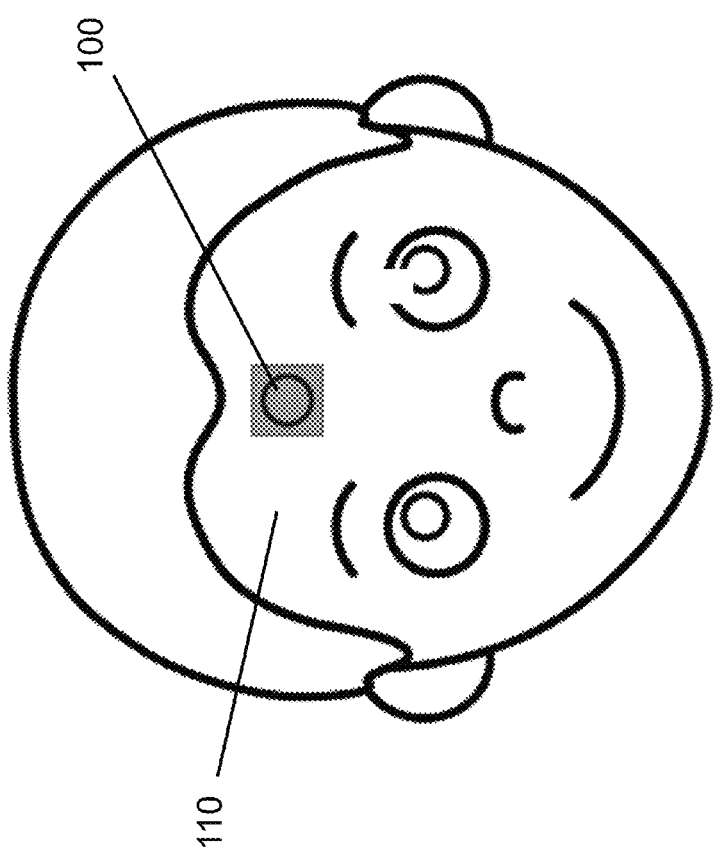
FIG. 1 illustrates the usage of a wearable electronic patch that is attached to a user's skin.

Referring to FIG. 1, an electronic patch 100 adheres to a user's skin 110 for measuring body vital signs. The electronic patch 100 can be placed on forehead, hand, wrist, arm, shoulder, waist, leg, foot, or other parts of the body. In the present application, the term "electronic patch" can also be referred to as "electronic sticker" or "electronic tag".

As discussed above, wearable electronic patches face several challenges: the user's skin 110 may interfere with their proper operations. For example, the electronic patch 100 may include an antenna for wireless communications with other devices. The antenna's communication range can be significantly reduced when an antenna is placed in contact with the user's skin 110. In one example, the wireless communication range of an antenna in contact with the skin is less than half the range if the antenna is placed just 4 mm away from the user's skin. In addition, while some sensors (e.g. for EEG and body temperature measurements) need to be in contact of users' skins 110 to conduct measurements, other sensors such as ambient temperature sensor are required to measure signals away from the user's skin 110.

Furthermore, people's daily activities such as taking showers or bathes, swimming, exercises, holding weights, etc. involve muscle and skin movements. The electronic patches thus need to responsively change their physical dimensions to be able to adhere to the skin for extended periods of time. The electronic patches may also be rubbed by clothing, hands, or other objects numerous times a day. While Band-Aid patches usually cannot on skin for more than a week, conventional electronic patches normally have much stiffer substrates, which makes them more easily rubbed off than Band-Aid stickers. Because drawbacks in this areas, some conventional electronic patches are not comfortable to wear because they are not stretchable, inflexible, and not breathable.

In some embodiments, the presently disclosure aims to overcome the drawbacks in conventional electronic patches, and to provide highly stretchable, compliant, durable, and comfortable wearable electronic patches while performing intended sensing and communication functions at and away user's skins.

Figure 2:
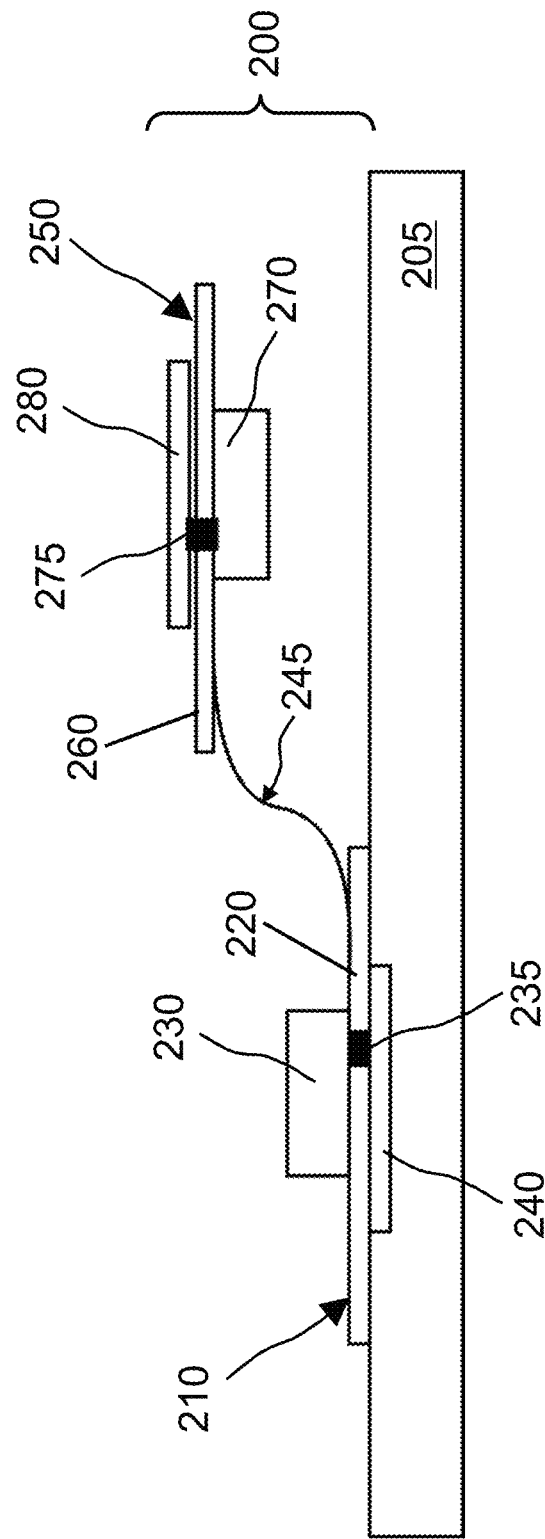
FIG. 2 illustrates two inter-connected electronic patches that are positioned at different distances from a user's skin in accordance with some embodiments of the present invention.

One solution to the above mentioned challenges is to provide functions in two inter-connected electronic patches positioned at different distances from user's skin. Referring to FIG. 2, an electronic patch assembly 200 includes an electronic patch 210 that is attached to a user's skin 205 and a second electronic patch 210 that is positioned at a distance away from the user's skin 205. The electronic patch 210 includes a substrate 220, a sensor 230 on the substrate 220, and a sensing pad 240 under the substrate 220. The sensing pad 240 can be in contact with the user's skin 205 and is electrically connected to the sensor 230 by a conductive pin 235. The electronic patch 250 includes a substrate 260, a sensor 270 under the substrate 260, and a sensing pad 280 on the substrate 260 and facing away from the user's skin 205. The sensing pad 280 is electrically connected to the sensor 270 by a conductive pin 275. The sensors 230 and 270 are electrically connected by a conductive line 245. The substrates 220 and 260 can be made elastic materials.

In one application, the sensor 230 and the sensing pad 240 can measure body temperature of the user, while the sensor 270 and the sensing pad 280 can measure ambient temperature. An insulating pad or spacer (not shown) can be disposed between the user's skin 205 and the sensor 270 to insulate ambient temperature measurement from the user's body heat. While the electronic patch assembly 200 can perform some intended functions, it requires two inter-connected electronic patches. The conductive line between the two electronic patches can easily be broken during user's body movements.

In some embodiments, the presently disclosure also provide simple structure and convenient manufacturing process for stretchable, compliant, durable, and comfortable wearable electronic patches that can perform intended sensing, actuation, and communication functions at and away user's skins.

Figure 3A:
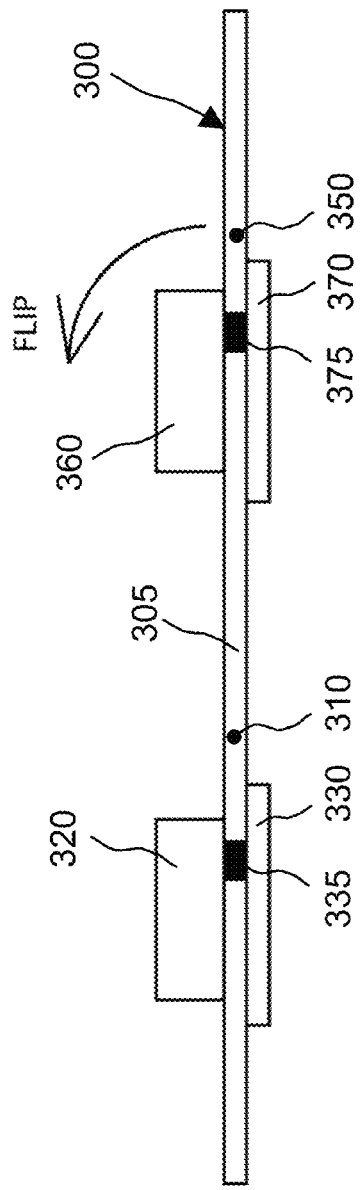
FIGS. 3A and 3B are respectively a cross-sectional and a top view of an exemplified flat flexible circuit substrate in preparation for a three-dimensional wearable electronic patch.
Figure 3B:
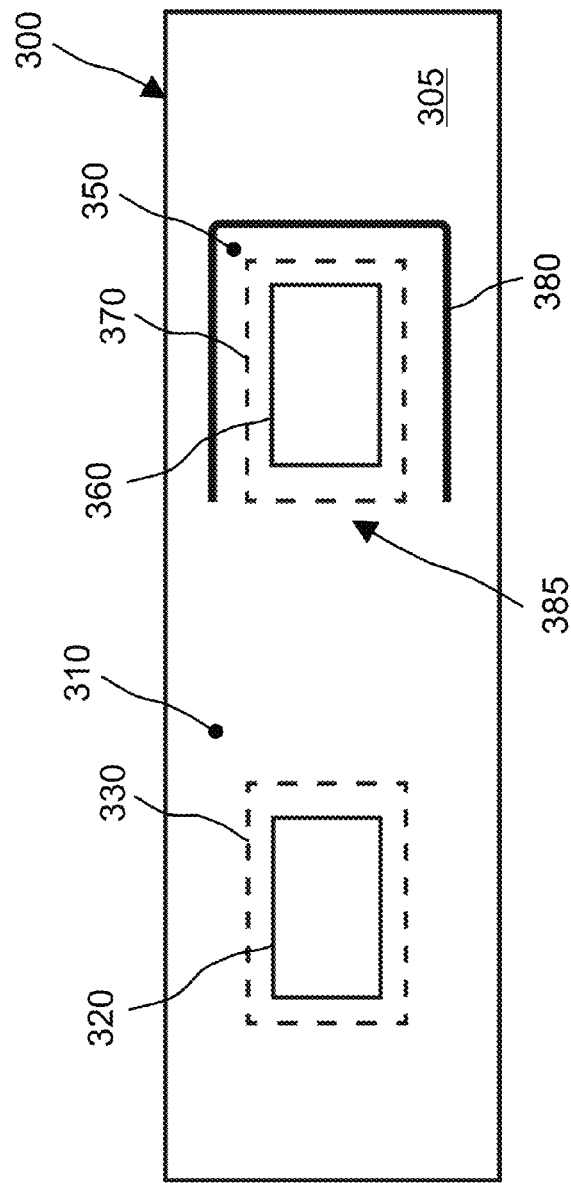

Referring to FIGS. 3A and 3B, a flat flexible circuit substrate 300 includes an elastic layer 305 that includes a first portion 310 and a second portion 350. A sensor 320 is mounted on the first portion 310 of the elastic layer 305, while a sensing pad 330 is bonded under the first portion 310 of the elastic layer 305. The sensing pad 330 is electrically connected to the sensor 320 by a conductive pin 335 through the elastic layer 305.

The second portion 350 of the elastic layer 305 is defined by cut(s) 380 along two or more sides and is connected to the first portion 310 on at least one side 385. The cut(s) 380, as described below, allow the second portion 350 to be partially lifted off the elastic layer 305 and flip over the first portion 310 of the elastic layer 305.

A sensor 360 is mounted on the second portion 350 of the elastic layer 305, while a sensing pad 370 is bonded under the second portion 350 of the elastic layer 305. The sensing pad 370 is electrically connected to the sensor 360 by a conductive pin 375 through the elastic layer 305. The sensors 320 and 360 are electrically connected by an electric circuit (not shown) embedded or on the elastic layer 305.

The elastic layer 305 is made of a non-conductive material such as an elastomeric material or a viscoelastic polymeric material. The elastic layer 205 can be made of a material having low Young's modulus and high failure strain. In some embodiments, the elastic layer 305 has a Young's Modulus <0.3 Gpa. In some cases, the elastic layer 305 and can have Young's Modulus <0.1 Gpa to provide enhanced flexibility and tackability. Materials suitable for the elastic layer 305 include elastomers, viscoelastic polymers, such as silicone, and medical grade polyurethane that is a transparent medical dressing used to cover and protect wounds with breathability and conformation to skin. On the other hand, the sensors 320 and 360 and the sensing pads 330, 370 are usually made more rigid materials. In some embodiments, the sensors 320 and 360 and the sensing pads 330, 370 can have Young's Modulus larger than 0.5 Gpa, such as in a range between 1.0 Gpa-10 Gpa.

Figure 4A:
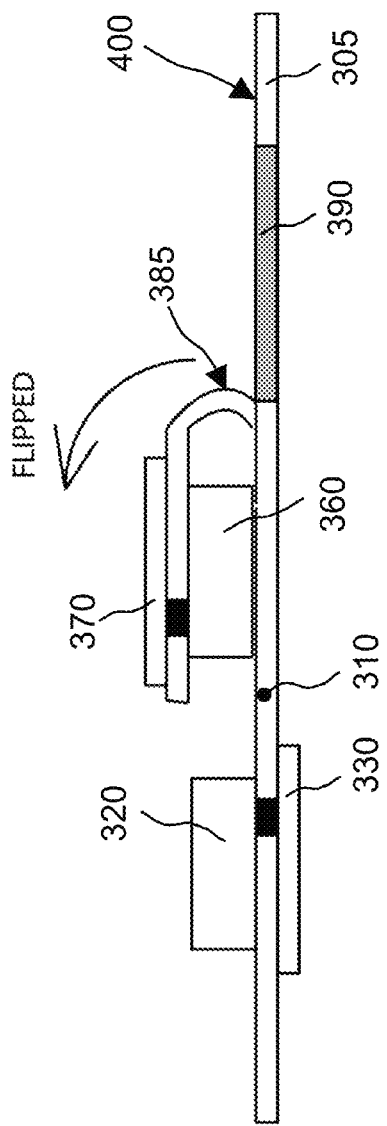
FIG. 4A is a cross-sectional view of a three-dimensional wearable electronic patch prepared using the flat flexible circuit substrate in FIGS. 3A and 3B in accordance with some embodiments of the present invention.
Figure 4B:
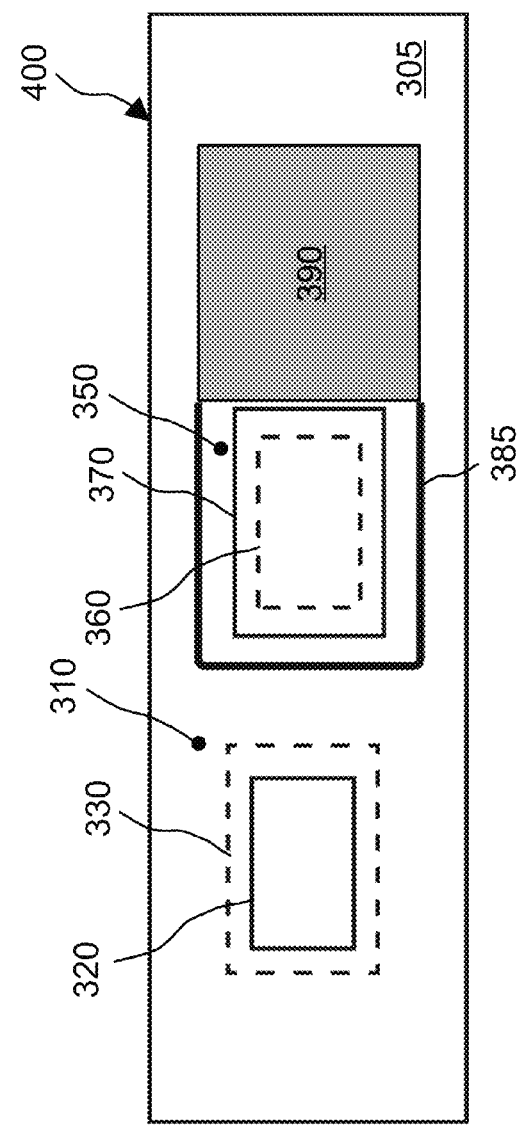
FIG. 4B is a top view of the three-dimensional wearable electronic patch in FIG. 4A in accordance with some embodiments of the present invention.

The flat flexible circuit substrate 300 is used to as an intermediate preparatory structure for making a three-dimensional electronic patch 400, as shown in FIGS. 4A and 4B. The second portion 350 of the elastic layer 305 is lifted up by opening the cut(s) 380, and flipped such that the sensor 360 is positioned on or above the first portion 310 of the elastic layer 305. An adhesive can be applied on the sensor 360 to allow it to adhere to the first portion 310 of the elastic layer 305. The sensing pad 370 is now on the second portion 350 and facing away from the first portion 310. The sensing pad 370 can be in parallel to the first portion 310. The side 385 stays connected to the rest of the elastic layer 305. The lifting and flipping of the second portion 350 leaves a void 390 in the elastic layer 305.

The three-dimensional electronic patch 400 can be used to sense signals at and away from a user's skin. In one application, the sensing pad 330 and the lower surface of the first portion 310 of the elastic layer 305 are in contact of a user's skin. An adhesive layer can be applied under the elastic layer 305 to help stick to the user's skin. The adhesive layer can be pressure sensitive, which allows the compliant wearable patches tightly adhere to human skin under pressure, applied for example by a thumb. For instance, the adhesive layer can be made of a medical pressure sensitive adhesive. An example of such adhesive is medical grade tackified Hypoallergenic Pressure Sensitive Adhesive. The sensor 320 and the sensing pad 330 can measure body temperature. The sensor 360 and the sensing pad 370 can measure ambient temperature. Since the sensing pad 370 is spaced apart from the user's skin, the ambient temperature sensing is not or little affected by the heat from the user's body.

In some embodiments, the skin temperature measure measured by the sensor 330 can be calibrated and corrected by the ambient temperature measured by the sensor 360 because skin temperature often varies in response to ambient temperature. The difference between the two temperatures measured by the sensors 330 and 360 can be used to extrapolate the true temperature within the core of the user's body.

In some embodiments, referring to FIGS. 5A and 5B, a flat flexible circuit substrate 500 includes an elastic layer 505 that includes a first portion 510 and a second portion 550. A sensor 520 is mounted on the first portion 510 of the elastic layer 505, while a sensing pad 530 is bonded under the first portion 510 of the elastic layer 505. The sensing pad 530 is electrically connected to the sensor 520 by a conductive pin 535 through the elastic layer 505.

The second portion 550 of the elastic layer 505 is defined by cut(s) 580 along two or more sides and is connected to the first portion 510 on at least one side 585. The cut(s) 580, as described below, allows the second portion 550 to be lifted up and flip over the first portion 510 of the elastic layer 505.

A spacer 560 is mounted on the second portion 550 of the elastic layer 505. A conductive circuit such as an antenna circuit 570 is bonded under or embedded within the second portion 550 of the elastic layer 505. The antenna circuit 570 can include conductive line disposed in several wounds (e.g. in a helical shape). The antenna circuit 570 and the sensor 520 are electrically connected by an electric circuit (not shown) embedded or on the elastic layer 505.

The elastic layer 505 is made of a non-conductive material such as an elastomeric material or a viscoelastic polymeric material. The elastic layer 205 can be made of a material having low Young's modulus and high failure strain. In some embodiments, the elastic layer 505 has Young's Modulus <0.3 Gpa. In some cases, the elastic layer 505 and can have Young's Modulus <0.1 Gpa to provide enhanced flexibility and tackability. Materials suitable for the elastic layer 505 include elastomers, viscoelastic polymers, such as silicone, and medical grade polyurethane that is a transparent medical dressing used to cover and protect wounds with breathability and conformation to skin. On the other hand, the sensors 520, the sensing pad 530, and the antenna circuit 570 are usually made more rigid materials. In some embodiments, the sensors 520, the sensing pad 530, and the antenna circuit 570 can have Young's Modulus larger than 0.5 Gpa, such as in a range between 1.0 Gpa-10 Gpa.

Figure 6A:
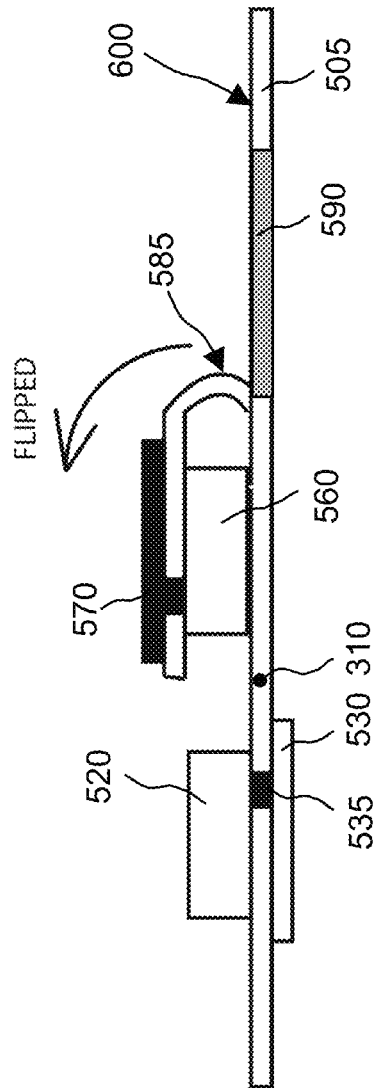
FIG. 6A is a cross-sectional view of a three-dimensional wearable electronic patch prepared using the flat flexible circuit substrate in FIGS. 5A and 5B in accordance with some embodiments of the present invention.
Figure 6B:
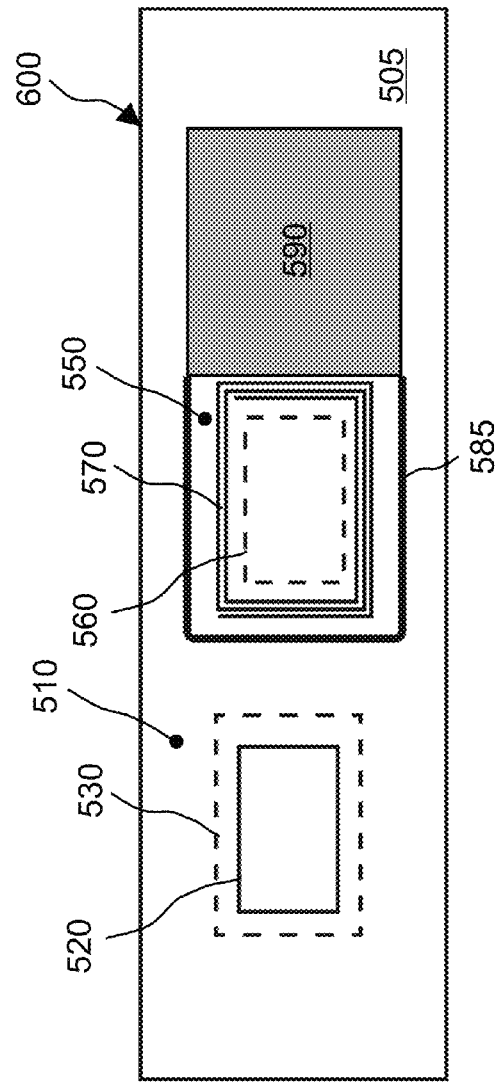
FIG. 6B is a top view of the three-dimensional wearable electronic patch in FIG. 6A in accordance with some embodiments of the present invention.

The flat flexible circuit substrate 500 is used to as an intermediate preparatory structure for making a three-dimensional electronic patch 600, as shown in FIGS. 6A and 6B. The second portion 550 of the elastic layer 505 is lifted up by opening the cut(s) 580, and flipped such that the spacer 560 is positioned on or above the first portion 510 of the elastic layer 505. The side 585 stays connected to the rest of the elastic layer 505. The lifting and flipping of the second portion 550 leaves a void 590 in the elastic layer 505.

An adhesive can be applied on the sensor 560 to allow it to adhere to the first portion 510 of the elastic layer 505. The antenna circuit 570 is now on the second portion 550 and facing away from the first portion 510, thus minimizing interference from the user's skin as well as from other components in the three-dimensional electronic patch 600. The antenna circuit 570 can substantially parallel to the first portion 510 or to the user's skin.

The three-dimensional electronic patch 600 can be used to sense signals at a user's skin while transmitting wireless signals from an antenna away from the user's skin. The sensing pad 530 and the lower surface of the first portion 510 of the elastic layer 505 are in contact of a user's skin. An adhesive layer can be applied under the elastic layer 505 to help stick to the user's skin. The adhesive layer can be pressure sensitive, which allows the compliant wearable patches tightly adhere to human skin under pressure, applied for example by a thumb. For instance, the adhesive layer can be made of a medical pressure sensitive adhesive. An example of such adhesive is medical grade tackified Hypoallergenic Pressure Sensitive Adhesive.

For example, the sensor 520 and the sensing pad 530 can measure body temperature, EEG signals, pulse signal, and other body vital signals. The antenna circuit 570 can transmit wireless signals to other devices. The thickness of the spacer 560 can be adjusted to minimize the interference of user's body to wireless transmissions. As discussed above, the radial range of wireless communication of the three-dimensional electronic patch 600 can double by keeping the antenna circuit 570 at 4 mm away from the user's skin in comparison to a conventional electronic patch in which the antenna circuit 570 being positioned near the user's skin.

The antenna circuit 570, along with other components (such as an amplifier, a transceiver, a processor etc.) can communicate with external devices based on NFC standard, RFID, Wi-Fi, Bluetooth, or other types of wireless communication standard. Examples of external devices include smart phones, computers, mobile payment devices, scanners and readers (e.g. RFID readers), medical devices, security systems, personal identification systems, etc. Wireless communications compatible with the electronic patch 200 include NFC in a frequency range near 13.56 MHz, UHF RFID at about 915 MHz, Bluetooth in 2.4 GHz or 5 GHz frequency ranges, and so on.

For example, the antenna circuit 570 can transmit wireless signals to transfer sensing data measured by the sensor 520 to other devices, as well as receive commands from other devices.

The three-dimensional electronic patches 400, 600 can also include electronic components such as the semiconductor chips, resistors, capacitors, inductors, diodes (including for example photo sensitive and light emitting types), sensors, transistors, amplifiers. The sensors can also measure temperature, acceleration and movements, and chemical or biological substances. The electronic components can also include electromechanical actuators, chemical injectors, etc. The semiconductor chips can perform communications, logic, signal or data processing, control, calibration, status report, diagnostics, and other functions.

The presently disclosed three-dimensional wearable electronic patches can provide sensing and communication functions away from the users' skins in addition to sensing and other functions in contact from users' skins. An advantage of the presently disclosed three-dimensional wearable electronic patch is that they can be easily manufactured from flat flexible circuit substrates instead of having to assemble multiple electronic patches. In one implementation, the disclosed three-dimensional wearable electronic patches can be packaged and shipped in flat configurations; the second portion can be partially lifted off and folded in the field to prepare the three dimensional structure.

The presently disclosed three-dimensional wearable electronic patches are flexible and stretchable thus providing durability and more comfort to the users.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination.

Only a few examples and implementations are described. Other implementations, variations, modifications and enhancements to the described examples and implementations may be made without deviating from the spirit of the present invention. For example, the applications and the types of electronic components of the disclosed electronic patches are not limited by the examples given above; they can include other functions such as other types of sensing (pressure, vibration, acceleration, electrical, magnetic, optical, etc.), communications, fluid delivery, heat production, mechanical actuations, and so on. Other vital body signals can be measured in addition to the examples given above.

The foldable portion of the elastic layer can have other shapes and configurations without deviating from the present invention. The sensors, antenna, and spacers associated with the foldable portion of the elastic layer can be disposed at different positions relative to the foldable portion of the elastic layer as well as relative to other components in un-folded portions of the elastic layer.

What is claimed is:

1. A three-dimensional electronic patch, comprising:
  a flat flexible circuit substrate, comprising:
    an elastic layer including a first portion and a second portion,
    wherein the second portion includes at least one side connected to the first portion of the elastic layer and one or more sides defined by one or more cuts in the elastic layer;
    a first sensor on the first portion of the elastic layer; and
    a conductive layer positioned at the second portion of the elastic layer and in electrical connection with the first sensor, wherein the second portion is folded to position the conductive layer away from the first portion.

2. The three-dimensional electronic patch of claim 1, wherein the folded second portion is substantially parallel to the first portion of the elastic layer, wherein the folded second portion is at a distance away from the first portion of the elastic layer.

3. The three-dimensional electronic patch of claim 2, further comprising:
  a spacer between the first portion of the elastic layer and the folded second portion of the elastic layer, wherein the spacer is configured to keep the folded second portion at a distance away from the first portion of the elastic layer.

4. The three-dimensional electronic patch of claim 3, further comprising:
  an adhesive layer configured to bond the spacer to the elastic layer.

5. The three-dimensional electronic patch of claim 1, further comprising:
  a first conductive sensing pad under the first portion of the elastic layer and in electrical connection with the first sensor.

6. The three-dimensional electronic patch of claim 5, wherein the first conductive sensing pad and the conductive layer of the folded second portion are respectively on opposing sides of the three-dimensional electronic patch.

7. The three-dimensional electronic patch of claim 5, wherein the first conductive sensing pad is configured to be in contact with a user's skin, wherein the first sensor is configured to measure body temperature of a user via the first conductive sensing pad.

8. The three-dimensional electronic patch of claim 5, wherein the first conductive sensing pad and the first sensor are electrically connected by a conduct pin through the first portion of the elastic layer.

9. The three-dimensional electronic patch of claim 1, further comprising:
  a second sensor at the second portion of the elastic layer and in electrical connection with the conductive layer, wherein the conductive layer includes a second conductive sensing pad electrically connected with the second sensor.

10. The three-dimensional electronic patch of claim 9, wherein the second sensor is configured to measure ambient temperature via the second conductive sensing pad.

11. The three-dimensional electronic patch of claim 9, wherein the second conductive sensing pad and the second sensor are electrically connected by a conductive pin through the second portion of the elastic layer.

12. The three-dimensional electronic patch of claim 9, further comprising:
  an adhesive layer configured to bond the second sensor to the first portion of the elastic layer.

13. The three-dimensional electronic patch of claim 1, wherein the conductive layer comprises an antenna circuit.

14. The three-dimensional electronic patch of claim 13, wherein the antenna circuit is electrically connected with the first sensor by a circuit in or on the elastic layer.

15. The three-dimensional electronic patch of claim 13, wherein the antenna circuit is configured to transmit wireless signals to transfer sensing data measured by the first sensor.

16. A three-dimensional electronic patch, comprising:
  a flat flexible circuit substrate, comprising:
    an elastic layer including a first portion and a second portion,
    wherein the second portion includes at least one side connected to the first portion of the elastic layer and one or more sides defined by one or more cuts in the elastic layer;
    a first sensor on the first portion of the elastic layer; and
    a conductive layer positioned at the second portion of the elastic layer and in electrical connection with the first sensor, wherein the second portion is lifted off to position the conductive layer away from rest of the elastic layer including the first portion.

17. The three-dimensional electronic patch of claim 16, further comprising:
   a first conductive sensing pad under the first portion of the elastic layer and in electrical connection with the first sensor.

18. The three-dimensional electronic patch of claim 17, wherein the first conductive sensing pad is configured to be in contact with a user's skin, wherein the first sensor is configured to measure body temperature of a user via the first conductive sensing pad.

19. The three-dimensional electronic patch of claim 16, further comprising:
   a second sensor at the second portion of the elastic layer and in electrical connection with the conductive layer, wherein the conductive layer includes a second conductive sensing pad electrically connected with the second sensor.

20. The three-dimensional electronic patch of claim 19, wherein the second sensor is configured to measure ambient temperature via the second conductive sensing pad.

21. The three-dimensional electronic patch of claim 16, wherein the conductive layer comprises an antenna circuit.

* * * * *